United States Patent [19]

Fabricius et al.

[11] Patent Number: 4,517,293

[45] Date of Patent: May 14, 1985

[54] HIGH YIELD PROCESS FOR IN VITRO PRODUCTION OF SERUM-FREE AND MITOGEN-FREE INTERLEUKIN-2 USING A ROLLER BOTTLE CULTURE SYSTEM

[75] Inventors: Hans-Åke Fabricius, Breisach; Roland Stahn, Holzhausen, both of Fed. Rep. of Germany

[73] Assignee: Hooper Trading Co. N.V., Curacao,

[21] Appl. No.: 576,894

[22] Filed: Feb. 3, 1984

Related U.S. Application Data

[60] Division of Ser. No. 418,378, Sep. 15, 1982, Pat. No. 4,448,879, which is a continuation-in-part of Ser. No. 247,769, Mar. 26, 1981, Pat. No. 4,390,623, which is a continuation-in-part of Ser. No. 193,112, Oct. 2, 1980, abandoned.

[51] Int. Cl.$^3$ ............................................. C12P 21/00
[52] U.S. Cl. .......................................... 435/68; 435/2; 435/241; 435/286; 435/312
[58] Field of Search ............... 435/241, 286, 296, 312, 435/68, 2

[56] References Cited

U.S. PATENT DOCUMENTS 3,812,016 5/1974 Muller .................................. 435/312
4,337,104 6/1982 Lynn ..................................... 435/296

Primary Examiner—Sam Rosen
Attorney, Agent, or Firm—Sherman & Shalloway

[57] ABSTRACT

An improved in vitro cell culture process for producing in high yield and purity a serum-free and mitogen-free interleukin-2-containing conditioned supernatant. The incubation steps during stimulation and conditioning of the interleukin-2 producing cells is carried out with a rapidly rotating roller bottle culture system. Yields of interleukin-2 are on the order of 10-fold and higher than obtained by similar cultivations carried out in flat dishes or tubes or in a roller bottle culture system rotated at conventional speeds. Improvement in yields in both the static and roller culture systems are also achieved by incubating the IL-2 producing cells under high oxygen concentrations, for example atmospheres of at least 70% $O_2$ and at least 5% $CO_2$. In addition to using peripheral mononuclear blood cells (PBL) as the source of leukocytes containing the IL-2 producer cells, it is also possible to use buffy coat cells which are readily available as a waste by-product from blood banks.

4 Claims, No Drawings

HIGH YIELD PROCESS FOR IN VITRO PRODUCTION OF SERUM-FREE AND MITOGEN-FREE INTERLEUKIN-2 USING A ROLLER BOTTLE CULTURE SYSTEM

This is a division of application Ser. No. 418,378, filed Sept. 15, 1982, which is now U.S. Pat. No. 4,448,879 which is a continuation-in-part of our prior copending application Ser. No. 247,769, filed Mar. 26, 1981, which is now U.S. Pat. No. 4,390,623 issued June 28, 1983, which in turn is a continuation-in-part of application Ser. No. 193,112, filed Oct. 2, 1980, and now abandoned.

This invention relates to an improved method for producing T-cell growth factor (TCGF), also known as Interleukin-2 (IL-2) in an in vitro culture system. More particularly, this invention relates to improvements in the in vitro culture production method for producing serum-free and mitogen-free interleukin-2 preparations disclosed in the above mentioned prior applications Ser. No. 193,112 and Ser. No. 247,769, the disclosures of which are incorporated herein, in their entirety, by reference thereto; specifically this invention relates to the use of a roller bottle culture system for improving the yield of interleuken-2. This invention also relates to a further improvement wherein the cultivation is carried out under high oxygen concentration.

There has been an extensive amount of research in recent years regarding the immunopotentiating effects of various lymphokines, including interleukin-2. In July 1980, an International Workshop on Interleukin-2 was held in Geisenheim, West-Germany and a symposium publication based on this meeting was published in Behring Institute Mitteilunger, No. 67, December 1980.

Murine and human Interleukin-2 have been partially purified and characterized as described for instance by S. A. Rosenberg, et al "In Vitro Growth of Murine T Cells. III. Method for Separation of T Cell Growth Factor (TCGF) From Concanavalin A and Biological Activity of the Resulting TCGF", J. of Immunological Methods, 33 (1980), pp. 339-350; J. Watson, et al "T-Cell Growth Factors: Interleukin-2", Immunology Today, December 1980, pp. 113-116; D. Mochizuki, et al, "Biochemical and Biological Characterization of Lymphocyte Regulatory Molecules. IV. Purification of Interleukin 2 from a Murine T Cell Lymphoma", J. of Immunology, Vol. 125, No. 6, (Dec. 1980), pp. 2579-2583; J. W. Mier and R. C. Gallo "Purification and Some Characteristics of Human T-Cell Growth Factor (TCGF) From PHA-Stimulated Lymphocyte Conditioned Media".

The immunopotentiating effects of lymphokines, especially interleukin-2 have been described by several researchers, including, for example, Papermaster, et al "Preliminary Observations on Tumor Regressions Induced By Local Administration of a Lymphoid Cell Culture Supernatant Fraction in Patients With Cutaneous Metastatic Lesions", J. of Immunology and Immunopathology, Vol. 5, pp. 31-47 (1976); Henney, et al "Interleukin-2 Augments Natural Killer Cell Activity", Nature Vol. 291, May 28, 1981, pp. 335-338; Lotze, et al., "The In Vivo Distribution of Autologous Human and Murine Lymphoid Cells Grown in T Cell Growth Factor (TCGF): Implications for The Adoptive Immunotherapy of Tumors", J. of Immunology, Vol. 12, No. 4 (October 1980). The inventors own clinical studies have demonstrated the lack of any harmful side effects by the in vivo administration of interleukin-2 in tumor patients.

The importance of serum-free tissue culture systems has been recognized by several authors, for example, see B. W. Needleman and J. M. Weiler, "Human Lymphocyte Transformation Induced by Mitogens And Antigens In A Serum-Free Tissue Culture System", J. of Immunological Methods, 44 (1981), pp. 3-14; H. S. Warren and R. G. Pembrey, "A Method For The Production And Quantitative Assay Of Human Lymphokine Preparations", J. of Immunological Methods, 41 (1981), pp. 9-21.

Production of a lectin-free murine interleukin-2 preparation is described by P. J. Spiess and S. A. Rosenberg, "A Simplified Method For The Production Of Murine T-Cell Growth Factor Free Of Lectin", J. of Immunological Methods, 42 (1981), pp. 13-222.

However, to date, it has not been possible to produce Interleukin-2 on a large scale in culture systems nor has there been any successful efforts to produce Interleukin-2 synthetically or by genetic engineering.

Attempts to optimize the yield of Interleukin-2 in vitro cell cultures systems has largely centered on, for example, optimization of type of and mitogen concentration, cell number and cell type, and other similar factors. See, for example, Jose M. Alvarez, et al "Human T Cell Growth Factor I. Optimal Conditions For Its Production", J. of Immunology, Vol. 123, No. 3 (Sept. 1979), pp. 977-983. While some degree of success has been achieved by these methods, still greater yields would be highly beneficial to the study and applications of Interleukin-2, particularly for long term and commercial use.

In "Regression of Cutaneous Neoplasms Following Delayed-Type Hypersensitivity Challenge Reactions to Microbial Antigens or Lymphokines", by O. A. Holtermann, et al, J. of Medicine, Vol. 6, No. 2, 1975, pp. 157,168, the authors report that they produced lymphokines from mitogen sensitized peripheral blood cells which were incubated on a roller drum at 37° C. However, no further details of the incubation step using the roller drum are reported. Normally, when cultivation on roller drums is used, the drum is rotated at rates of about 1 to 6 revolutions per minute.

In conventional culture systems, e.g. flat dish, culture tube, or culture bottle, the cells being cultured tend to accumulate quickly at the bottom of the respective culture vessel. Cell accumulation in the in vitro production of Interleukin-2 (IL-2) appears to result during the mitogen (e.g. PHA) stimulation step when the cells tend to become "sticky" and clump together. This cell accumulation results in:

(1) rapid nutritional depletion of the lower layer of the culture medium;

(2) accumulation of metabolic products and synthesized proteins (some of which may be toxic or suppressive in respect to IL-2 production);

(3) intensive cell-to-cell contact, again possibly resulting in suppression of IL-2 production by specific suppressor cells.

Media conditioned in such "conventional" systems, i.e. where cells are allowed to settle and where no circulation of the medium is provided, require concentration, on the order of 5 to 10-fold, to yield IL-2 levels high enough for the in vitro growth of cytotoxic IL-2 dependent T-cells. In fact, some batches require even higher concentration, while others show no activity at all.

It can, therefore, be appreciated that IL-2 production in these conventional culture systems is both generally low and highly unpredictable. This situation is highly undesireable where it is needed to produce IL-2 on a commercial scale. In addition, the conventional culture systems, especially the use of flat culture dishes, e.g. Petri dishes, require long production times and have high space and volume requirements to obtain useful yields of IL-2, because of the large number of plastic dishes required. Similar space and volume requirements exist with culture tube systems.

Another economic drawback in the conventional culture systems as presently practiced for production of interleukin-2 from human sources is the high cost of obtaining the peripheral mononuclear blood cells and the resulting waste of the non-used portions of the starting whole blood supply.

It has also been found by the present inventors that in the large scale production of interleukin-2 by in vitro culture systems, in which the medium in the culture vessels form layers, often in excess of several inches, a substantial barrier to oxygen diffusion (from the air of the air/$CO_2$ mixture in the incubator) into the liquid media is presented. In fact, liquid layers in excess of 3 to 5 millimeters show some significant barrier to oxygen penetration throughout the thickness of the liquid conditioning media.

These and other drawbacks are now avoided by the various embodiments of the present invention which are all improvements over the static in vitro cell culture system described in our copending applications Ser. No. 193,112 and Ser. No. 247,769.

Accordingly, in one aspect, the present invention provides a process in which the peripheral mononuclear blood cells (PBL) are packed on a porous support (e.g. nylon wool, sepharose gel, hollow fiber systems, etc.) and the liquid cell culture medium and atmosphere are recirculated throughout the incubation and replenished with fresh culture medium by diafiltration. The recirculation of only the culture fluids tends to prevent depletion of the nutrients in the lower layer of the culture medium and removes metabolic and synthesized products from the cell environment.

In a more preferred embodiment of the invention directed toward prevention of cell clumping or accumulation and its deleterious side effects the incubation in both the stimulating and conditioning steps is performed in a rapidly rotating roller bottle culture system.

The roller culture system avoids all of the above mentioned drawbacks resulting from cell accumulation, including the cell-to-cell contact which is not particularly addressed by the first mentioned embodiment. Thus, the rapidly rotating culture bottle system provides:

(1) intensive mixing by the roller action to assure a completely homogeneous culture medium during the whole conditioning and stimulating periods and thereby prevents local depletion;

(2) dispersion of metabolic products and synthesized proteins throughout the whole culture volume, thereby resulting in only a slow and largely insignificant buildup of possibly toxic or suppressive product concentrations;

(3) maintenance of uniform cell suspension thereby preventing suppression resulting from cell-to-cell contact.

Other advantages of the roller culture system include the capability of handling large volumes of culture medium permitting production of up to several 1000 liters—on a pilot plant scale-of highly active IL-2 conditioned media; relatively low costs due to reusable bottles, low space and volume requirements, and handling of large unfractionated volumes. In fact, for in vitro growth of IL-2 dependent cytotoxic T-cells, it is often unnecessary to concentrate the conditioned media, although concentration of the conditioned media by only 2 to 5-fold is preferred.

In another aspect of the invention, especially useful for large scale production, in both static (e.g. flat dish) and dynamic (i.e. roller bottle) culture systems the yield of IL-2 is improved 5 to 10-fold or more by carrying out the incubation steps under high oxygen concentrations, in particular with gaseous mixtures containing from about 70 to 95% oxygen, 5 to 15% carbon dioxide, and the remainder primarily nitrogen. In static culture systems the long diffusion distances for oxygen in the relatively deep liquid cell culture medium is compensated for by the higher oxygen concentration resulting in increased concentrations of IL-2 which are typically 5 times higher than the yields obtained in a conventional air/$CO_2$ gas mixture.

In the roller culture system, the presence of high oxygen concentrations provide reliably high yields and oxygen concentrations of IL-2 in the conditioned media allowing the conditioned media to be diluted up to 50 times, preferably up to 5 to 10 times, for the in vitro growth of cytotoxic T-cells. In comparison, IL-2 conditioned media produced in roller culture with a normal air/$CO_2$ atmosphere have to be concentrated 0 to 5-fold to support growth of IL-2 dependent cytotoxic T-cells. This is, of course, still a significant improvement over the static culture systems.

Even in the embodiment using a porous support with packed cells instead of the roller culture, the higher oxygen concentration provides increased yields of IL-2 and offers the advantage of a more easily controlled oxygen supply by continuously oxygenating and otherwise reconditioning (e.g. pH, nutrients, product removal, etc.) the cell-free circulating culture medium.

In still another aspect of the invention, applicable to each of the above described embodiments, the economics of the process are substantially improved by using buffy coat cells for the peripheral mononuclear blood cells. Buffy coat cells have the advantage that they are obtained as a by-product from whole blood which has been treated to recover whole blood plasma and erythrocytes (red blood cells) and do not require addition of heparin to prevent blood clotting. Thus, the buffy coat cells which are normally discarded can be recovered at substantially no additional cost over the normal production of red blood cells and whole blood plasma from blood banks. Moreover, the recovery of leukocytes is higher from buffy-coat cells than from PBL obtained by the procedures described in our prior applications and which are well known in the art.

The above and other objects of the invention are achieved in a first embodiment in which serum-free and mitogen-free interleukin-2 containing supernatant is produced by (1) stimulating IL-2 producing primary cells which have been washed to remove substantially all serum proteins bound to the external cell membrane surface by incubating the washed cells in a liquid tissue culture medium supplemented with serum protein and a mitogen in a roller bottle culture system which is caused to rotate at a speed sufficient to provide a homogeneous culture medium, disperse metabolic products and synthesized proteins throughout the culture medium, and maintain a uniform cell suspension in the culture medium; (2) separating and washing the stimulated cells to remove substantially all of the serum protein and mitogen; and (3) conditioning the cells obtained in step (2) by incubating the cells in the presence of a serum-protein-free and mitogen-free liquid tissue culture medium in a roller bottle culture system which is caused to rotate at a speed sufficient to provide a homogeneous culture medium, disperse metabolic products and synthesized proteins throughout the culture medium, and maintain a uniform cell suspension in the culture medium, to thereby transfer interleukin-2 into the liquid phase. Generally, for a bottle having a diameter of 4 to 5 inches, a roller speed of at least 20 r.p.m., corresponding to about 6 revolutions per minute of the bottle itself, is sufficient to obtain the objectives of the invention. As in our original method the stimulation and conditioning incubation steps are carried out for periods of about 4 to 8 hours and 18 to 24 hours, respectively.

According to a preferred mode of this embodiment, as described in the above-mentioned prior applications, the liquid tissue culture medium from which the stimulated cells have been separated are recycled to stimulate subsequent batches of cells, and the conditioned cells separated from the tissue culture medium are also recycled for restimulation.

According to the procedure described in our previous applications, the incubations during stimulation and conditioning are carried out under static conditions. That is, the cells and liquid tissue culture medium supplemented with serum and mitogen in the case of the stimulation step and the cells in the presence of the serum-free and mitogen-free liquid tissue culture medium in the case of the conditioning step are simply placed in a suitable container, such as a Petri-dish, and placed in the incubator where they are incubated at a temperature of about 37° C. with an air/$CO_2$-mixture containing 5 to 10% $CO_2$.

It has now been discovered that when the cells are cultured in the static vessel, the interleukin-2 producing cells tend to clump together, thereby reducing the number of available cells for producing interleukin-2; at the same time the concentration of IL-2 tends to be substantially higher in the bottom part of the still-standing culture vessel and, therefore, there is a greater tendency for consumption of the so-produced interleukin-2 to be adsorbed on cells in the culture vessel carrying receptors for interleukin-2.

In order to avoid the clumping phenomenon and to obtain a more uniform concentration of interleukin-2 throughout the culture vessel, it was attempted to utilize a roller culture system, using a conventional roller culture machine making from 1 to 6 revolutions per minute. However, operating at these conventional speeds did not prevent the cells during the mitogen (e.g. phytohemagglutinin-PHA) stimulation from becoming "sticky" and clumping together. Using a four inch diameter bottle, it was found that the cells producing lymphokines still clumped together at speeds of rotation as high as 15 r.p.m.

In accordance with the present invention, clumping of the cells in the roller culture vessel is totally or substantially totally eliminated by modifying the rollers of the roller culture system to make at least 20 revolutions per minute (corresponding to about 6 revolutions for a 5 inch diameter bottle). The serum and mitogen-free culture supernatants have a ten-fold and higher increase in yield of interleukin-2 when produced by the modification of the previously disclosed method wherein the incubation during the stimulating and conditioning steps is performed in a roller culture system which is caused to rotate at at least 20 r.p.m.

It has also been discovered that even further improvements in yield of interleukin-2 in the culture supernatants can be achieved by modifying the surface of the roller bottle to remove any irregularities in its surface. It has been found that such irregularities in the surface of the roller bottle, which is typically made from glass material, tend to tear up the cells including the interleukin-2 producer cells. The smoothing of the roller surface has been successfully achieved by providing a thin silicone coating on the roller surface. Thus, in the absence of the siliconization of the roller in the roller culture vessel some 30 to 50% of the starting peripheral mononuclear blood cells are lost during the PHA stimulation whereas only some 15 to 30% of the cells are destroyed after siliconization of the roller culture vessel.

In a second embodiment of the invention improved yields of IL-2 are obtained by (1) stimulating IL-2 producing primary cells which have been washed to remove substantially all serum proteins bound to the external cell membrane surface by incubating the cells in a liquid tissue culture medium supplement with serum protein and mitogen under an oxygen-rich atmosphere comprising from about 70 to about 95% oxygen and from about 5 to 15% carbon monoxide (the remainder bieng primarily nitrogen with minor amounts of other inert gases normally found in air); (2) separating and washing the stimulated cells to remove substantially all of the serum protein and mitogen; and (3) conditioning the cells obtained in step (2) by incubating the cells in the presence of a serum protein-free and mitogen-free liquid tissue culture medium under an oxygen rich atmosphere as described in step (1).

This embodiment using an oxygen rich atmosphere during the incubation (stimulation and conditioning) steps can be applied to the roller culture system of the first mentioned embodiment, or to a static, e.g. flat dish, tube, or non-rotating bottle, culture system. Recirculation of both the liquid tissue culture culture medium and the conditioned cells is also applicable to this embodiment.

In a preferred mode of carrying out the above described second embodiment of the invention as applied especially to the first embodiment the IL-2 producing cells are buffy-coat cells obtained as a by-product during the separation of red blood cells and plasma from whole blood by conventional techniques. According to this embodiment the buffy-coat cells should be substantially fresh, e.g. no more than 2 to 3 hours old, when used in production of interleukin-2.

The invention will now be described in greater detail for a better understanding thereof with the aid of the following non-limiting examples.

The roller cultivation apparatus can be any conventional device for rolling bottles containing tissue culture medium and cells. Such apparatus is widely used in the field of biology, especially in virology for the production of viruses. However, these devices normally operate at relatively low speeds, on the order of from about 1 to 6 r.p.m. The device must, therefore, be modified to operate at higher speeds of at least about 20 r.p.m.

Typically, a roller cultivation apparatus will include at least one pair, and preferably two to four pairs of horizontally disposed parallel rollers spaced apart a short distance sufficient to allow the roller culture bottle to rest on both rollers of a pair. Rotation of one or both rollers of a pair causes rotation of the bottle in contact therewith. The direction of rotation is unimportant.

One arrangement of the apparatus which has been found useful includes three parallel rollers which can accommodate two bottles. All three rollers can be rotated or only the outer two can be driven and the middle roller can be freely rotating. It is also possible for only the middle roller to be driven and the outer two freely rotating. Two or more sets of the three rollers can be provided in stacked relationship so long as sufficient clearance is provided between the rows to accommodate the diameter of the bottle.

As stated above, these roller culture devices are normally designed to impart a rotation to the rollers of only 1 to 6 r.p.m.

Studies by the inventors have shown that at these speeds clumping of the sticky cells cannot be avoided. By modifying the apparatus to produce roller speeds as high as 15 r.p.m. it was still not possible to overcome the clumping phenomenon. However, by further modifying the apparatus to produce roller speeds of at least 20 r.p.m. it becomes possible to prevent the sticky interleukin-2 producing cells from forming agglomerates with the attendant disadvantages thereof.

The upper limit of the roller speed is not particularly critical but should not be so high as to cause rupture or breakdown of the cells. Usually roller speeds up to about 50 r.p.m. are satisfactory and no particular advantage is obtained by operating at higher speeds. Generally, roller speeds on the order of about 20 to 50 r.p.m. preferably 22 to 40 r.p.m., which correspond, for roller bottles ranging in diameter from 4 to 5 inches and containing from about 50 to 200 ml of culture medium, to roller bottle rotations of from about 5 to about 20 r.p.m., preferably from about 5 to 15 r.p.m., are sufficient to avoid clumping of the sticky cells.

For larger or smaller size roller bottles, larger or smaller concentrations of cells and amounts of culture medium, different amounts of rolling friction between the rollers and roller bottles, different diameters of the rollers, etc., the minimum rotation speed of the rollers to effect sufficient mixing to assure complete homogeniety of the culture medium, dispersion of metabolic and synthesized products, and maintenance of uniform cell suspension, can be readily determined by simple experimentation.

It is preferred, especially when the roller bottle vessels are to be repeatedly used for stimulating and conditioning the cells, to avoid formation of surface irregularities. For example, the roller bottles are made of glass. After several washings, the surfaces of these bottles become rough and irregular tending to tear the cells up. One means for preventing the roughening of the glass surface is to coat it with a silicon solution. Such procedure is known in the art.

For example, one suitable siliconizing solution is commercially available under the tradename "Siliconlosung Serva", article number 35130 IIIa, available from Serva, Heidelberg, Federal Republic of Germany. A small volume of silicone solution is poured into the roller bottle. When the inner surface has been completely covered by silicone, excess solution is decanted off. The bottle is dried at room temperature with the nozzle downwards. The remaining film of silicone is now burned into the glass by heating the bottle for 1 hour at 100°–150° C. The treated bottle has a very smooth surface which is hydrophobic and it may be used for 5 to 10 times before a new siliconization procedure will be necessary. The siliconization treatment is important to reduce loss of cells during stimulation and conditioning.

The cultivation process using rolling bottles may be essentially the same in all other aspects as in the process described in our prior applications, e.g. Ser. No. 247,769. Thus, the IL-2 producing cells may be any normal (i.e. non-cancer or non-tumor) primary cell system such as peripheral mononuclear blood lymphocytes which are obtained and washed as previously described. The cell donor may be sheep, pig, cattle or human. The temperature and atmosphere may also be those previously and conventionally used, e.g. 37° C. and an air/5–15% $CO_2$ atmosphere.

However, for best results in terms of economy and yields of interleukin-2, particularly in applications for human use, the IL-2 producing cells can be buffy coat cells and the atmosphere should be oxygen enriched, for example 70–95% $O_2$, preferably 80–95% $O_2$ (percent by volume), with about 5 to 5%, preferably 5 to 10% carbon dioxide ($CO_2$) as a buffer, and the remainder is substantially nitrogen, with a minor amount of inert gases, such as argon, normally found in air.

EXAMPLE 1

As a specific example of the roller bottle culture process peripheral mononuclear blood cells are first obtained as previously described. Briefly, human blood obtained from a blood bank is mixed with heparin, a clotting inhibitor. The blood is layered into Ficoll-hypaque mixture-containing sterile tubes which are then centrifuged. The resulting layer of peripheral mononuclear blood cells formed above the Ficoll-hypaque layer in each tube is drawn off carefully with a pipet. The cells are then pooled in a clean tube and diluted with, for example RPMI 1640. The tube is centrifuged at speeds which do not rupture the cells and the supernatant is discarded. The cells are then washed repeatedly with fresh portions of RPMI solutions in the same manner. The resulting washed cell pellet containing about 500–1000 million cells is diluted with about 5 to 10 ml RPMI 1640 solution.

The cells may then be seeded out at a density of about $3 \times 10^6$/ml in a tissue culture medium, e.g. RPMI 1640 containing about 4 micrograms of phytohemagglutinin (PHA) supplemented with 10–15% blood serum. In place of the blood serum, the plasmatic human interleukin-2 inducing protein (PHILIP) described in the co-pending U.S. application Ser. No. 255,251, filed Apr. 17, 1981, which issued on Sept. 27, 1983 as U.S. Pat. No. 4,406,830 the disclosure of which is incorporated herein by reference thereto, may be used.

At this point, the cell- and lectin-containing culture medium is transferred to roller culture bottles. Bottles ranging in diameter of from 4 to 5 inches are used and each bottle is filled with from 50 to 200 ml of culture medium. The roller bottles, after being filled with an air/$CO_2$ (5–10%) mixture, are placed in an incubator equipped with the roller apparatus. The temperature in the incubator is maintained at about 37° C. The rollers are rotated at about 25 r.p.m. (a roller bottle speed of about 6 r.p.m.) and the cells are incubated for about 4 to 8 hours, preferably about 4 hours.

Thereafter, the bottles are removed from the incubator, and the stimulated cells containing culture medium is decanted into centrifuge tubes, and the cells sedimented and washed three times in the conventional manner as previously described, and then seeded out into fresh culture medium, again at a cell density of about 3,000,000/ml. In this case, the cell containing culture medium, which is not supplemented with PHA or serum proteins, is again transferred into the roller bottles in 50 to 200 ml portions and incubated under the same conditions used in the stimulation step except that the time of the conditioning incubation is increased to about 18 to 24 hours, preferably about 20 hours.

Thereafter, the medium is again transferred from the roller bottles to centrifuge tubes and processed as in our previous application (see Example 1 of Ser. No. 247,769). The cells can be reutilized in subsequent PHA restimulation and reconditioning for at least 5 additional cycles.

EXAMPLE 2

Example 1 is repeated except that the incubation in the stimulation and conditioning steps is performed under an atmosphere containing 90% $O_2$, 5% $CO_2$ and 5% $N_2$.

The interleukin-2 activity of the conditioned culture supernatants from the roller bottle plus air/$CO_2$ mixture, from the roller bottle plus 90% $O_2$, and from conventional PHA stimulation in 50 ml Falcon blue cap plastic tubes with normal atmospheric oxygen (air)+10% $CO_2$ (Comparative Example 1) were tested (three replications each) and the results are shown in the follow table:

| IL-2 ACTIVITY IN CONDITIONED CULTURE SUPERNATANTS | | | |
|---|---|---|---|
| | Preparation Procedure | | |
| | Plastic Tubes + air/$CO_2$ (Comp. Ex. 1) | Roller bottles + air/$CO_2$ (Ex. 1) | Roller bottles + 90% $O_2$ (Ex. 2) |
| cells per well × $10^{-3}$ (dilution factor) | 95 ± 12* (1:4) | * | 243 ± 27* (1:8) |

*Average of 3 experiments

COMPARATIVE EXAMPLES 2-3

Examples 1 and 2 are repeated except that the rollers were rotated at speeds of only about 15 r.p.m. The results are substantially the same as Comparative Example 1 and substantial cell clumping is observed.

Example 3

Example 2 is repeated except that buffy coat cells are used in place of the PBL cells. The buffy coat cells are obtained as follows: Blood is collected in a vessel containing a preservative for the erythrocytes, e.g. ACD (Adenine, citrate, dextrose) which is a standard solution for preserving erythrocytes. The use of heparin, which is needed for the interleukin-2 production in whole blood conserves is not necessary. After collection, the fresh blood specimen is centrifuged at 1000 to 1500×G for 20 minutes. The erythrocytes will sediment and the leukocytes will form a thin layer (buffy-coat) on the erythrocyte sediment. Thereafter, the buffy-coat is aspirated off the erythrocyte layer and used for the production of interleukin-2. The leuko- and erythrocyte-free plasma can be collected and used, for example, for industrial purposes or for the infusion as whole plasma into patients. The sedimented erythrocytes can be used for clinical purposes (e.g. blood transfusion) as usual. Most blood banks prepare erthrocyte-concentrates in the way described above only with the difference that the buffy-coat is not collected. The leukocytes are generally considered worthless. The blood conserve usually stands in a refrigerator for some day or weeks before it is used. During this time, the leukocytes will die. Using these buffy-coat cells, it is possible to get raw material for the interleukin-2 production almost without additional costs for the blood bank.

When the leukocytes are now processed for IL-2 production, they are separated from contaminating erythrocytes and thrombocytes by a Ficoll-hypaque gradient in exactly the same manner as previously described. The cell number recovered will usually be about 20% higher than the cell number recovered from a heparin-conserve. It is very important that the buffy-coat cells are absolutely fresh, when they are stimulated for the IL-2 production. They should not be older than 2 to 3 hours. It has been found, quite unexpectedly that the use of buffy-coat has one limitation: If one tries to produce IL-2 in buffy-coats under normal oxygen concentration, no sufficient production will be found. One prerequisite, therefore, is the use of an oxygen rich atmosphere in the same manner previously described. The result obtained are substantially the same as in Example 2.

COMPARATIVE EXAMPLE 4

When example 2 is repeated except that buffy-coat cells are use in place of the PBL cells, substantially no IL-2 production is observed. This example shows that buffy coat cells require high oxygen concentrations during incubation, although the reason for this has not been fully elucidated.

The interleukin-2 containing supernatants obtained by the improved procedures of this invention, after filtering e.g. on an Amicon YM-10 filter as described in our prior applications, is a highly purified product. Product purity of the interleukin-2 containing conditioned supernatant, can be demonstrated by comparison of the biological activity with the protein content. Biological activity of such interleukin-2 containing preparations can be detected in material diluted up to 50 times before filtering on an Amicon YM-10 filter. After filtering, the biological activity can be multiplied by a factor which is identical with the reduction of the sample volume during the filtration process. An interleukin-2 containing supernatant which before filtering has a biological activity which is detectable in 50 fold dilution and which is concentrated by filtration to a tenth of its original volume will after the filtration have a biological activity detectable in a 1:500 dilution. The protein content of the filtered supernatants usually ranges from 5 to 20 μg/ml, due to the inherent differences in cell loss from cell batch to cell batch. Also, the cells of each donor have inherently different capacities to produce IL-2 by mitogen stimulation.

Accordingly, it is recognized that the present invention provides significant improvements in yield and in the overall economy of the inventor's original procedure for the in vitro production of high purity serum-free and mitogen- (e.g. lectin-free interleukin-2 containing conditioned supernatants. These supernatants are useful in the treatment of patients having depressed natural killer cell function or having depressed T cell function, in the diagnosis and treatment of immune deficiency in tumor patients, and in general for any of the utilities previously disclosed in application Ser. No. 247,769, or by other authors.

What we claim is:

1. A process for producing a serum-free and mitogen-free interleukin-2 containing supernatant comprising:
   (1) stimulating IL-2 producing primary cells which have been washed to remove substantially all proteins bound to the external cell membrane surface by incubating the washed cells in a liquid tissue culture medium supplemented with serum protein and a mitogen in a roller bottle cultivation system which is caused to rotate at a speed sufficient to rotate said roller bottle at from about 5 to 20 revolutions per minute to thereby provide a homogeneous culture medium, disperse metabolic products and synthesized proteins throughout the culture medium, and maintain a uniform cell suspension in the culture medium;
   (2) separating and washing the stimulated cells to remove substantially all of the serum and mitogen; and
   (3) conditioning the cells obtained in step (2) by incubating the cells in the presence of a serum-free and mitogen-free liquid tissue culture medium in a roller bottle cultivation system which is caused to rotate at a speed sufficient to rotate said roller bottle at from about 5 to 20 revolutions per minute to thereby provide a homogeneous culture medium, disperse metabolic products and synthesized proteins throughout the culture medium, and maintain a uniform cell suspension in the culture medium to thereby transfer interleukin-2 into the liquid phase.

2. The process of claim 1 wherein the incubation in the stimulating and the conditioning steps is performed in an atmosphere comprising from 70 to 95% oxygen and from 5 to 15% $CO_2$.

3. The process of claim 1 or 2 wherein the starting IL-2 producing primary cells are buffy-coat cells obtained from a human donor.

4. The process of claim 1 wherein the roller bottles have a diameter of from about 4 to about 5 inches and are filled with from about 50 to 200 milliliters of the liquid tissue culture medium, and wherein the roller bottles in the stimulation and conditioning incubation steps are rotated by the rollers of the roller bottle culture system at a speed of at least 6 revolutions per minute.

* * * * *